United States Patent [19]
Jacobs et al.

[11] Patent Number: 5,969,093
[45] Date of Patent: Oct. 19, 1999

[54] SECRETED PROTEINS

[75] Inventors: Kenneth Jacobs, Newton; Kerry Kelleher, Marlborough; McKeough Carlin, Cambridge; John M. McCoy, Reading, all of Mass.

[73] Assignee: Genetics Institute, Inc., Cambridge, Mass.

[21] Appl. No.: 08/833,823

[22] Filed: Apr. 10, 1997

Related U.S. Application Data

[62] Division of application No. 08/514,014, Aug. 11, 1995.

[51] Int. Cl.$^6$ ..................... C07K 14/00
[52] U.S. Cl. ............ 530/300; 530/350; 536/23.1; 536/23.5; 435/69.1
[58] Field of Search ................ 530/300, 350; 536/23.1, 23.5; 435/69.1

*Primary Examiner*—Rebecca E. Prouty
*Assistant Examiner*—Nashaat T. Nashed
*Attorney, Agent, or Firm*—Scott A. Brown; Suzanne A. Sprunger; Thomas J. DesRosier

[57] ABSTRACT

Novel polynucleotides and the proteins encoded thereby are disclosed.

16 Claims, 4 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
    (A) LENGTH: 2209 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 38..1447

(xi) SEQUENCE DESCRIPTION: SEQ ID NO:1:

```
GAGAAGATAA AACTGGACAC TGGGGAGACA CAACTTC ATG CTG CGT GGG ATC TCC         55
                                        Met Leu Arg Gly Ile Ser
                                         1               5

CAG CTA CCT GCA GTG GCC ACC ATG TCT TGG GTC CTG CTG CCT GTA CTT         103
Gln Leu Pro Ala Val Ala Thr Met Ser Trp Val Leu Leu Pro Val Leu
             10                  15                  20

TGG CTC ATT GTT CAA ACT CAA GCA ATA GCC ATA AAG CAA ACA CCT GAA         151
Trp Leu Ile Val Gln Thr Gln Ala Ile Ala Ile Lys Gln Thr Pro Glu
         25                  30                  35

TTA ACG CTC CAT GAA ATA GTT TGT CCT AAA AAA CTT CAC ATT TTA CAC         199
Leu Thr Leu His Glu Ile Val Cys Pro Lys Lys Leu His Ile Leu His
     40                  45                  50

AAA AGA GAG ATC AAG AAC AAC CAG ACA GAA AAG CAT GGC AAA GAG GAA         247
Lys Arg Glu Ile Lys Asn Asn Gln Thr Glu Lys His Gly Lys Glu Glu
 55                  60                  65                  70

AGG TAT GAA CCT GAA GTT CAA TAT CAG ATG ATC TTA AAT GGA GAA GAA         295
Arg Tyr Glu Pro Glu Val Gln Tyr Gln Met Ile Leu Asn Gly Glu Glu
                 75                  80                  85

ATC ATT CTC TCC CTA CAA AAA ACC AAG CAC CTC CTG GGG CCA GAC TAC         343
Ile Ile Leu Ser Leu Gln Lys Thr Lys His Leu Leu Gly Pro Asp Tyr
             90                  95                 100

ACT GAA ACA TTG TAC TCA CCC AGA GGA GAG GAA ATT ACC ACG AAA CCT         391
Thr Glu Thr Leu Tyr Ser Pro Arg Gly Glu Glu Ile Thr Thr Lys Pro
         105                 110                 115

GAG AAC ATG GAA CAC TGT TAC TAT AAA GGA AAC ATC CTA AAT GAA AAG         439
Glu Asn Met Glu His Cys Tyr Tyr Lys Gly Asn Ile Leu Asn Glu Lys
     120                 125                 130

AAT TCT GTT GCC AGC ATC AGT ACT TGT GAC GGG TTG AGA GGA TAC TTC         487
Asn Ser Val Ala Ser Ile Ser Thr Cys Asp Gly Leu Arg Gly Tyr Phe
135                 140                 145                 150

ACA CAT CAT CAC CAA AGA TAC CAG ATA AAA CCT CTG AAA AGC ACA GAC         535
Thr His His His Gln Arg Tyr Gln Ile Lys Pro Leu Lys Ser Thr Asp
                 155                 160                 165

GAG AAA GAA CAT GCC GTC TTT ACA TCT AAC CAG GAG GAA CAA GAC CCA         583
Glu Lys Glu His Ala Val Phe Thr Ser Asn Gln Glu Glu Gln Asp Pro
             170                 175                 180

GCT AAC CAC ACA TGT GGT GTG AAG AGC ACT GAC GGG AAA CAA GGC CCA         631
Ala Asn His Thr Cys Gly Val Lys Ser Thr Asp Gly Lys Gln Gly Pro
         185                 190                 195

ATT CGA ATC TCT AGA TCA CTC AAA AGC CCA GAG AAA GAA GAC TTT CTT         679
Ile Arg Ile Ser Arg Ser Leu Lys Ser Pro Glu Lys Glu Asp Phe Leu
```

```
                200                    205                     210
CGG GCA CAG AAA TAC ATT GAT CTC TAT TTG GTG CTG GAT AAT GCC TTT        727
Arg Ala Gln Lys Tyr Ile Asp Leu Tyr Leu Val Leu Asp Asn Ala Phe
215                 220                 225                 230

TAT AAG AAC TAT AAT GAG AAT CTA ACT CTG ATA AGA AGC TTT GTG TTT        775
Tyr Lys Asn Tyr Asn Glu Asn Leu Thr Leu Ile Arg Ser Phe Val Phe
                235                 240                 245

GAT GTG ATG AAC CTA CTC AAT GTG ATA TAT AAC ACC ATA GAT GTT CAA        823
Asp Val Met Asn Leu Leu Asn Val Ile Tyr Asn Thr Ile Asp Val Gln
            250                 255                 260

GTG GCC TTG GTA GGT ATG GAA ATC TGG TCT GAT GGG GAT AAG ATA AAG        871
Val Ala Leu Val Gly Met Glu Ile Trp Ser Asp Gly Asp Lys Ile Lys
            265                 270                 275

GTG GTG CCC AGC GCA AGC ACC ACG TTT GAC AAC TTC CTG AGA TGG CAC        919
Val Val Pro Ser Ala Ser Thr Thr Phe Asp Asn Phe Leu Arg Trp His
280                 285                 290

AGT TCT AAC CTG GGG AAA AAG ATC CAC GAC CAT GCT CAG CTT CTC AGC        967
Ser Ser Asn Leu Gly Lys Lys Ile His Asp His Ala Gln Leu Leu Ser
295                 300                 305                 310

GGG ATT AGC TTC AAC AAT CGA CGT GTG GGA CTG GCA GCT TCA AAT TCC       1015
Gly Ile Ser Phe Asn Asn Arg Arg Val Gly Leu Ala Ala Ser Asn Ser
                315                 320                 325

TTG TGT TCC CCA TCT TCG GTT GCT GTT ATT GAG GCT AAA AAA AAG AAT       1063
Leu Cys Ser Pro Ser Ser Val Ala Val Ile Glu Ala Lys Lys Lys Asn
            330                 335                 340

AAT GTG GCT CTT GTA GGA GTG ATG TCA CAT GAG CTG GGC CAT GTC CTT       1111
Asn Val Ala Leu Val Gly Val Met Ser His Glu Leu Gly His Val Leu
            345                 350                 355

GGT ATG CCT GAT GTT CCA TTC AAC ACC AAG TGT CCC TCT GGC AGT TGT       1159
Gly Met Pro Asp Val Pro Phe Asn Thr Lys Cys Pro Ser Gly Ser Cys
360                 365                 370

GTG ATG AAT CAG TAT CTG AGT TCA AAA TTC CCA AAG GAT TTC AGT ACA       1207
Val Met Asn Gln Tyr Leu Ser Ser Lys Phe Pro Lys Asp Phe Ser Thr
375                 380                 385                 390

TCT TGC CGT GCA CAT TTT GAA AGA TAC CTT TTA TCT CAG AAA CCA AAG       1255
Ser Cys Arg Ala His Phe Glu Arg Tyr Leu Leu Ser Gln Lys Pro Lys
                395                 400                 405

TGC CTG CTG CAA GCA CCT ATT CCT ACA AAT ATA ATG ACA ACA CCA GTG       1303
Cys Leu Leu Gln Ala Pro Ile Pro Thr Asn Ile Met Thr Thr Pro Val
            410                 415                 420

TGT GGG AAC CAC CTT CTA GAA GTG GGA GAA GAC TGT GAT TGT GGC TCT       1351
Cys Gly Asn His Leu Leu Glu Val Gly Glu Asp Cys Asp Cys Gly Ser
            425                 430                 435

CCT AAG GAG TGT ACC AAT CTC TGC TGT GAA GCC CTA ACG TGT AAA CTG       1399
Pro Lys Glu Cys Thr Asn Leu Cys Cys Glu Ala Leu Thr Cys Lys Leu
440                 445                 450

AAG CCT GGA ACT GAT TGC GGA GGA GAT GCT CCA AAC CAT ACC ACA GAG       1447
Lys Pro Gly Thr Asp Cys Gly Gly Asp Ala Pro Asn His Thr Thr Glu
455                 460                 465                 470

TGAATCCAAA AGTCTGCTTC ACTGAGATGC TACCTTGCCA GGACAAGAAC CAAGAACTCT     1507

AACTGTCCCA GGAATCTTGT GAATTTTCAC CCATAATGGT CTTTCACTTG TCATTCTACT     1567

TTCTATATTG TTATCAGTCC AGGAAACAGG TAAACAGATG TAATTAGAGA CATTGGCTCT     1627

TTGTTTAGGC CTAATCTTTC TTTTTACTTT TTTTTTTCTT TTTTCTTTTT TTTTAAAGAT     1687

CATGAATTTG TGACTTAGTT CTGCCCTTTG GAGAACAAAA GAAAGCAGTC TTCCATCAAA     1747

TCACCTTAAA ATGCACGGCT AAACTATTCA GAGTTAACAC TCCAGAATTG TTAAATTACA     1807

AGTACTATGC TTTAATGCTT CTTTCATCTT ACTAGTATGG CCTATAAAAA AATAATACC     1867
```

```
ACTTGATGGG TGAAGGCTTT GGCAATAGAA AGAAGAATAG AATTCAGGTT TTATGTTATT      1927

CCTCTGTGTT CACTTCGCCT TGCTCTTGAA AGTGCAGTAT TTTTCTACAT CATGTCGAGA      1987

ATGATTCAAT GTAAATATTT TTCATTTTAT CATGTATATC CTATACACAC ATCTCCTTCA      2047

TCATCATATA TGAAGTTTAT TTTGAGAAGT CTACATTGCT TACATTTTAA TTGAGCCAGC      2107

AAAGAAGGCT TAATGATTTA TTGAACCATA ATGTCAATAA AAACACAACT TTTGAGGCAA      2167

AAAAAAAAAA AAAAAAAAAA AAAAAAAAAA AAAAAAAAAA AA                        2209
```

(2) INFORMATION FOR SEQ ID NO:2:

(i) SEQUENCE CHARACTERISTICS:
        (A) LENGTH: 470 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Arg Gly Ile Ser Gln Leu Pro Ala Val Ala Thr Met Ser Trp
 1               5                  10                  15

Val Leu Leu Pro Val Leu Trp Leu Ile Val Gln Thr Gln Ala Ile Ala
             20                  25                  30

Ile Lys Gln Thr Pro Glu Leu Thr Leu His Glu Ile Val Cys Pro Lys
         35                  40                  45

Lys Leu His Ile Leu His Lys Arg Glu Ile Lys Asn Asn Gln Thr Glu
     50                  55                  60

Lys His Gly Lys Glu Glu Arg Tyr Glu Pro Glu Val Gln Tyr Gln Met
 65                  70                  75                  80

Ile Leu Asn Gly Glu Glu Ile Ile Leu Ser Leu Gln Lys Thr Lys His
                 85                  90                  95

Leu Leu Gly Pro Asp Tyr Thr Glu Thr Leu Tyr Ser Pro Arg Gly Glu
            100                 105                 110

Glu Ile Thr Thr Lys Pro Glu Asn Met Glu His Cys Tyr Tyr Lys Gly
        115                 120                 125

Asn Ile Leu Asn Glu Lys Asn Ser Val Ala Ser Ile Ser Thr Cys Asp
    130                 135                 140

Gly Leu Arg Gly Tyr Phe Thr His His Gln Arg Tyr Gln Ile Lys
145                 150                 155                 160

Pro Leu Lys Ser Thr Asp Glu Lys Glu His Ala Val Phe Thr Ser Asn
                165                 170                 175

Gln Glu Glu Gln Asp Pro Ala Asn His Thr Cys Gly Val Lys Ser Thr
            180                 185                 190

Asp Gly Lys Gln Gly Pro Ile Arg Ile Ser Arg Ser Leu Lys Ser Pro
        195                 200                 205

Glu Lys Glu Asp Phe Leu Arg Ala Gln Lys Tyr Ile Asp Leu Tyr Leu
    210                 215                 220

Val Leu Asp Asn Ala Phe Tyr Lys Asn Tyr Asn Glu Asn Leu Thr Leu
225                 230                 235                 240

Ile Arg Ser Phe Val Phe Asp Val Met Asn Leu Leu Asn Val Ile Tyr
                245                 250                 255

Asn Thr Ile Asp Val Gln Val Ala Leu Val Gly Met Glu Ile Trp Ser
            260                 265                 270

Asp Gly Asp Lys Ile Lys Val Val Pro Ser Ala Ser Thr Thr Phe Asp
        275                 280                 285

Asn Phe Leu Arg Trp His Ser Ser Asn Leu Gly Lys Lys Ile His Asp
    290                 295                 300
```

```
His Ala Gln Leu Leu Ser Gly Ile Ser Phe Asn Asn Arg Arg Val Gly
305                 310                 315                 320

Leu Ala Ala Ser Asn Ser Leu Cys Ser Pro Ser Ser Val Ala Val Ile
            325                 330                 335

Glu Ala Lys Lys Asn Asn Val Ala Leu Val Gly Val Met Ser His
            340                 345                 350

Glu Leu Gly His Val Leu Gly Met Pro Asp Val Pro Phe Asn Thr Lys
            355                 360                 365

Cys Pro Ser Gly Ser Cys Val Met Asn Gln Tyr Leu Ser Ser Lys Phe
            370                 375                 380

Pro Lys Asp Phe Ser Thr Ser Cys Arg Ala His Phe Glu Arg Tyr Leu
385                 390                 395                 400

Leu Ser Gln Lys Pro Lys Cys Leu Leu Gln Ala Pro Ile Pro Thr Asn
                405                 410                 415

Ile Met Thr Thr Pro Val Cys Gly Asn His Leu Leu Glu Val Gly Glu
                420                 425                 430

Asp Cys Asp Cys Gly Ser Pro Lys Glu Cys Thr Asn Leu Cys Cys Glu
            435                 440                 445

Ala Leu Thr Cys Lys Leu Lys Pro Gly Thr Asp Cys Gly Gly Asp Ala
450                 455                 460

Pro Asn His Thr Thr Glu
465                 470

(2) INFORMATION FOR SEQ ID NO:3:

(i) SEQUENCE CHARACTERISTICS:
        (A) LENGTH: 2582 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 52..2034

(xi) SEQUENCE DESCRIPTION: SEQ ID NO:3:

ATTTCTCAGC TCCAAGCATT AGGTAAACCC ACCAAGCAAT CCTAGCCTGT G ATG GCG          57
                                                        Met Ala
                                                          1

TTT GAC GTC AGC TGC TTC TTT TGG GTG GTG CTG TTT TCT GCC GGC TGT         105
Phe Asp Val Ser Cys Phe Phe Trp Val Val Leu Phe Ser Ala Gly Cys
        5                   10                  15

AAA GTC ATC ACC TCC TGG GAT CAG ATG TGC ATT GAG AAA GAA GCC AAC         153
Lys Val Ile Thr Ser Trp Asp Gln Met Cys Ile Glu Lys Glu Ala Asn
    20                  25                  30

AAA ACA TAT AAC TGT GAA AAT TTA GGT CTC AGT GAA ATC CCT GAC ACT         201
Lys Thr Tyr Asn Cys Glu Asn Leu Gly Leu Ser Glu Ile Pro Asp Thr
35                  40                  45                  50

CTA CCA AAC ACA ACA GAA TTT TTG GAA TTC AGC TTT AAT TTT TTG CCT         249
Leu Pro Asn Thr Thr Glu Phe Leu Glu Phe Ser Phe Asn Phe Leu Pro
                55                  60                  65

ACA ATT CAC AAT AGA ACC TTC AGC AGA CTC ATG AAT CTT ACC TTT TTG         297
Thr Ile His Asn Arg Thr Phe Ser Arg Leu Met Asn Leu Thr Phe Leu
            70                  75                  80

GAT TTA ACT AGG TGC CAG ATT AAC TGG ATA CAT GAA GAC ACT TTT CAA         345
Asp Leu Thr Arg Cys Gln Ile Asn Trp Ile His Glu Asp Thr Phe Gln
        85                  90                  95
```

```
AGC CAT CAT CAA TTA AGC ACA CTT GTG TTA ACT GGA AAT CCC CTG ATA        393
Ser His His Gln Leu Ser Thr Leu Val Leu Thr Gly Asn Pro Leu Ile
    100                 105                 110

TTC ATG GCA GAA ACA TCG CTT AAT GGG CCC AAG TCA CTG AAG CAT CTT        441
Phe Met Ala Glu Thr Ser Leu Asn Gly Pro Lys Ser Leu Lys His Leu
115                 120                 125                 130

TTC TTA ATC CAA ACG GGA ATA TCC AAT CTC GAG TTT ATT CCA GTG CAC        489
Phe Leu Ile Gln Thr Gly Ile Ser Asn Leu Glu Phe Ile Pro Val His
                135                 140                 145

AAT CTG GAA AAC TTG GAA AGC TTG TAT CTT GGA AGC AAC CAT ATT TCC        537
Asn Leu Glu Asn Leu Glu Ser Leu Tyr Leu Gly Ser Asn His Ile Ser
            150                 155                 160

TCC ATT AAG TTC CCC AAA GAC TTC CCA GCA CGG AAT CTG AAA GTA CTG        585
Ser Ile Lys Phe Pro Lys Asp Phe Pro Ala Arg Asn Leu Lys Val Leu
        165                 170                 175

GAT TTT CAG AAT AAT GCT ATA CAC TAC ATC TCT AGA GAA GAC ATG AGG        633
Asp Phe Gln Asn Asn Ala Ile His Tyr Ile Ser Arg Glu Asp Met Arg
180                 185                 190

TCT CTG GAG CAG GCC ATC AAC CTA AGC CTG AAC TTC AAT GGC AAT AAT        681
Ser Leu Glu Gln Ala Ile Asn Leu Ser Leu Asn Phe Asn Gly Asn Asn
195                 200                 205                 210

GTT AAA GGT ATT GAG CTT GGG GCT TTT GAT TCA ACG GTC TTC CAA AGT        729
Val Lys Gly Ile Glu Leu Gly Ala Phe Asp Ser Thr Val Phe Gln Ser
                215                 220                 225

TTG AAC TTT GGA GGA ACT CCA AAT TTG TCT GTT ATA TTC AAT GGT CTG        777
Leu Asn Phe Gly Gly Thr Pro Asn Leu Ser Val Ile Phe Asn Gly Leu
            230                 235                 240

CAG AAC TCT ACT ACT CAG TCT CTC TGG CTG GGA ACA TTT GAG GAC ATT        825
Gln Asn Ser Thr Thr Gln Ser Leu Trp Leu Gly Thr Phe Glu Asp Ile
        245                 250                 255

GAT GAC GAA GAT ATT AGT TCA GCC ATG CTC AAG GGA CTC TGT GAA ATG        873
Asp Asp Glu Asp Ile Ser Ser Ala Met Leu Lys Gly Leu Cys Glu Met
260                 265                 270

TCT GTT GAG AGC CTC AAC CTG CAG GAA CAC CGC TTC TCT GAC ATC TCA        921
Ser Val Glu Ser Leu Asn Leu Gln Glu His Arg Phe Ser Asp Ile Ser
275                 280                 285                 290

TCC ACC ACA TTT CAG TGC TTC ACC CAA CTC CAA GAA TTG GAT CTG ACA        969
Ser Thr Thr Phe Gln Cys Phe Thr Gln Leu Gln Glu Leu Asp Leu Thr
                295                 300                 305

GCA ACT CAC TTG AAA GGG TTA CCC TCT GGG ATG AAG GGT CTG AAC TTG       1017
Ala Thr His Leu Lys Gly Leu Pro Ser Gly Met Lys Gly Leu Asn Leu
            310                 315                 320

CTC AAG AAA TTA GTT CTC AGT GTA AAT CAT TTC GAT CAA TTG TGT CAA       1065
Leu Lys Lys Leu Val Leu Ser Val Asn His Phe Asp Gln Leu Cys Gln
        325                 330                 335

ATC AGT GCT GCC AAT TTC CCC TCC CTT ACA CAC CTC TAC ATC AGA GGC       1113
Ile Ser Ala Ala Asn Phe Pro Ser Leu Thr His Leu Tyr Ile Arg Gly
340                 345                 350

AAC GTG AAG AAA CTT CAC CTT GGT GTT GGC TGC TTG GAG AAA CTA GGA       1161
Asn Val Lys Lys Leu His Leu Gly Val Gly Cys Leu Glu Lys Leu Gly
355                 360                 365                 370

AAC CTT CAG ACA CTT GAT TTA AGC CAT AAT GAC ATA GAG GCT TCT GAC       1209
Asn Leu Gln Thr Leu Asp Leu Ser His Asn Asp Ile Glu Ala Ser Asp
                375                 380                 385

TGC TGC AGT CTG CAA CTC AAA AAC CTG TCC CAC TTG CAA ACC TTA AAC       1257
Cys Cys Ser Leu Gln Leu Lys Asn Leu Ser His Leu Gln Thr Leu Asn
            390                 395                 400

CTG AGC CAC AAT GAG CCT CTT GGT CTC CAG AGT CAG GCA TTC AAA GAA       1305
Leu Ser His Asn Glu Pro Leu Gly Leu Gln Ser Gln Ala Phe Lys Glu
        405                 410                 415
```

```
TGT CCT CAG CTA GAA CTC CTC GAT TTG GCA TTT ACC CGC TTA CAC ATT         1353
Cys Pro Gln Leu Glu Leu Leu Asp Leu Ala Phe Thr Arg Leu His Ile
    420                 425                 430

AAT GCT CCA CAA AGT CCC TTC CAA AAC CTC CAT TTC CTT CAG GTT CTG         1401
Asn Ala Pro Gln Ser Pro Phe Gln Asn Leu His Phe Leu Gln Val Leu
435                 440                 445                 450

AAT CTC ACT TAC TGC TTC CTT GAT ACC AGC AAT CAG CAT CTT CTA GCA         1449
Asn Leu Thr Tyr Cys Phe Leu Asp Thr Ser Asn Gln His Leu Leu Ala
                455                 460                 465

GGC CTA CCA GTT CTC CGG CAT CTC AAC TTA AAA GGG AAT CAC TTT CAA         1497
Gly Leu Pro Val Leu Arg His Leu Asn Leu Lys Gly Asn His Phe Gln
            470                 475                 480

GAT GGG ACT ATC ACG AAG ACC AAC CTA CTT CAG ACC GTG GGC AGC TTG         1545
Asp Gly Thr Ile Thr Lys Thr Asn Leu Leu Gln Thr Val Gly Ser Leu
                485                 490                 495

GAG GTT CTG ATT TTG TCC TCT TGT GGT CTC CTC TCT ATA GAC CAG CAA         1593
Glu Val Leu Ile Leu Ser Ser Cys Gly Leu Leu Ser Ile Asp Gln Gln
        500                 505                 510

GCA TTC CAC AGC TTG GGA AAA ATG AGC CAT GTA GAC TTA AGC CAC AAC         1641
Ala Phe His Ser Leu Gly Lys Met Ser His Val Asp Leu Ser His Asn
515                 520                 525                 530

AGC CTG ACA TGC GAC AGC ATT GAT TCT CTT AGC CAT CTT AAG GGA ATC         1689
Ser Leu Thr Cys Asp Ser Ile Asp Ser Leu Ser His Leu Lys Gly Ile
                535                 540                 545

TAC CTC AAT CTG GCT GCC AAC AGC ATT AAC ATC ATC TCA CCC CGT CTC         1737
Tyr Leu Asn Leu Ala Ala Asn Ser Ile Asn Ile Ile Ser Pro Arg Leu
            550                 555                 560

CTC CCT ATC TTG TCC CAG CAG AGC ACC ATT AAT TTA AGT CAT AAC CCC         1785
Leu Pro Ile Leu Ser Gln Gln Ser Thr Ile Asn Leu Ser His Asn Pro
                565                 570                 575

CTG GAC TGC ACT TGC TCG AAT ATT CAT TTC TTA ACA TGG TAC AAA GAA         1833
Leu Asp Cys Thr Cys Ser Asn Ile His Phe Leu Thr Trp Tyr Lys Glu
        580                 585                 590

AAC CTG CAC AAA CTT GAA GGC TCG GAG GAG ACC ACG TGT GCA AAC CCG         1881
Asn Leu His Lys Leu Glu Gly Ser Glu Glu Thr Thr Cys Ala Asn Pro
595                 600                 605                 610

CCA TCT CTA AGG GGA GTT AAG CTA TCT GAT GTC AAG CTT TCC TGT GGG         1929
Pro Ser Leu Arg Gly Val Lys Leu Ser Asp Val Lys Leu Ser Cys Gly
                615                 620                 625

ATT ACA GCC ATA GGC ATT TTC TTT CTC ATA GTA TTT CTA TTA TTG TTG         1977
Ile Thr Ala Ile Gly Ile Phe Phe Leu Ile Val Phe Leu Leu Leu Leu
            630                 635                 640

GCT ATT CTG CTA TTT TTT GCA GTT AAA TAC CTT CTC AGG TGG AAA TAC         2025
Ala Ile Leu Leu Phe Phe Ala Val Lys Tyr Leu Leu Arg Trp Lys Tyr
                645                 650                 655

CAA CAC ATT TAGTGCTGAA GGTTTCCAGA GAAAGCAAAT AAGTGTGCTT                 2074
Gln His Ile
    660

AGCAAAATTG CTCTAAGTGA AAGAACTGTC ATCTGCTGGT GACCAGACCA GACTTTTCAG       2134

ATTGCTTCCT GGAACTGGGC AGGGACTCAC TGTGCTTTTC TGAGCTTCTT ACTCCTGTGA       2194

GTCCCAGAGC TAAAGAACCT TCTAGGCAAG TACACCGAAT GACTCAGTCC AGAGGGTCAG       2254

ATGCTGCTGT GAGAGGCACA GAGCCCTTTC CGCATGTGGA AGAGTGGGAG GAAGCAGAGG       2314

GAGGGACTGG GCAGGGACTG CCGGCCCCGG AGTCTCCCAC AGGGAGGCCA TTCCCCTTCT       2374

ACTCACCGAC ATCCCTCCCA GCACCACACA CCCCGCCCCT GAAAGGAGAT CATCAGCCCC       2434

CACAATTTGT CAGAGCTGAA GCCAGCCCAC TACCCACCCC CACTACAGCA TTGTGCTTGG       2494

GTCTGGGTTC TCAGTAATGT AGCCATTTGA GAAACTTACT TGGGGACAAA GTCTCAATCC       2554
```

TTATTTTAAA TGAAAAAAAA AAAAAAAA                                                  2582

(2) INFORMATION FOR SEQ ID NO:4:

(i) SEQUENCE CHARACTERISTICS:
        (A) LENGTH: 661 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Phe Asp Val Ser Cys Phe Phe Trp Val Leu Phe Ser Ala
 1               5                  10                  15

Gly Cys Lys Val Ile Thr Ser Trp Asp Gln Met Cys Ile Glu Lys Glu
            20                  25                  30

Ala Asn Lys Thr Tyr Asn Cys Glu Asn Leu Gly Leu Ser Glu Ile Pro
            35                  40                  45

Asp Thr Leu Pro Asn Thr Thr Glu Phe Leu Glu Phe Ser Asn Phe
        50                  55                  60

Leu Pro Thr Ile His Asn Arg Thr Phe Ser Arg Leu Met Asn Leu Thr
 65                  70                  75                  80

Phe Leu Asp Leu Thr Arg Cys Gln Ile Asn Trp Ile His Glu Asp Thr
                85                  90                  95

Phe Gln Ser His His Gln Leu Ser Thr Leu Val Leu Thr Gly Asn Pro
               100                 105                 110

Leu Ile Phe Met Ala Glu Thr Ser Leu Asn Gly Pro Lys Ser Leu Lys
               115                 120                 125

His Leu Phe Leu Ile Gln Thr Gly Ile Ser Asn Leu Glu Phe Ile Pro
130                 135                 140

Val His Asn Leu Glu Asn Leu Glu Ser Leu Tyr Leu Gly Ser Asn His
145                 150                 155                 160

Ile Ser Ser Ile Lys Phe Pro Lys Asp Phe Pro Ala Arg Asn Leu Lys
                165                 170                 175

Val Leu Asp Phe Gln Asn Asn Ala Ile His Tyr Ile Ser Arg Glu Asp
                180                 185                 190

Met Arg Ser Leu Glu Gln Ala Ile Asn Leu Ser Leu Asn Phe Asn Gly
            195                 200                 205

Asn Asn Val Lys Gly Ile Glu Leu Gly Ala Phe Asp Ser Thr Val Phe
210                 215                 220

Gln Ser Leu Asn Phe Gly Gly Thr Pro Asn Leu Ser Val Ile Phe Asn
225                 230                 235                 240

Gly Leu Gln Asn Ser Thr Thr Gln Ser Leu Trp Leu Gly Thr Phe Glu
                245                 250                 255

Asp Ile Asp Asp Glu Asp Ile Ser Ser Ala Met Leu Lys Gly Leu Cys
            260                 265                 270

Glu Met Ser Val Glu Ser Leu Asn Leu Gln Glu His Arg Phe Ser Asp
            275                 280                 285

Ile Ser Ser Thr Thr Phe Gln Cys Phe Thr Gln Leu Gln Glu Leu Asp
            290                 295                 300

Leu Thr Ala Thr His Leu Lys Gly Leu Pro Ser Gly Met Lys Gly Leu
305                 310                 315                 320

Asn Leu Leu Lys Lys Leu Val Leu Ser Val Asn His Phe Asp Gln Leu
                325                 330                 335

Cys Gln Ile Ser Ala Ala Asn Phe Pro Ser Leu Thr His Leu Tyr Ile
            340                 345                 350
```

Arg Gly Asn Val Lys Lys Leu His Leu Gly Val Gly Cys Leu Glu Lys
          355                 360                 365

Leu Gly Asn Leu Gln Thr Leu Asp Leu Ser His Asn Asp Ile Glu Ala
      370                 375                 380

Ser Asp Cys Cys Ser Leu Gln Leu Lys Asn Leu Ser His Leu Gln Thr
385                 390                 395                 400

Leu Asn Leu Ser His Asn Glu Pro Leu Gly Leu Gln Ser Gln Ala Phe
              405                 410                 415

Lys Glu Cys Pro Gln Leu Glu Leu Leu Asp Leu Ala Phe Thr Arg Leu
          420                 425                 430

His Ile Asn Ala Pro Gln Ser Pro Phe Gln Asn Leu His Phe Leu Gln
          435                 440                 445

Val Leu Asn Leu Thr Tyr Cys Phe Leu Asp Thr Ser Asn Gln His Leu
      450                 455                 460

Leu Ala Gly Leu Pro Val Leu Arg His Leu Asn Leu Lys Gly Asn His
465                 470                 475                 480

Phe Gln Asp Gly Thr Ile Thr Lys Thr Asn Leu Leu Gln Thr Val Gly
              485                 490                 495

Ser Leu Glu Val Leu Ile Leu Ser Ser Cys Gly Leu Leu Ser Ile Asp
          500                 505                 510

Gln Gln Ala Phe His Ser Leu Gly Lys Met Ser His Val Asp Leu Ser
          515                 520                 525

His Asn Ser Leu Thr Cys Asp Ser Ile Asp Ser Leu Ser His Leu Lys
      530                 535                 540

Gly Ile Tyr Leu Asn Leu Ala Ala Asn Ser Ile Asn Ile Ile Ser Pro
545                 550                 555                 560

Arg Leu Leu Pro Ile Leu Ser Gln Gln Ser Thr Ile Asn Leu Ser His
              565                 570                 575

Asn Pro Leu Asp Cys Thr Cys Ser Asn Ile His Phe Leu Thr Trp Tyr
          580                 585                 590

Lys Glu Asn Leu His Lys Leu Glu Gly Ser Glu Glu Thr Thr Cys Ala
          595                 600                 605

Asn Pro Pro Ser Leu Arg Gly Val Lys Leu Ser Asp Val Lys Leu Ser
610                 615                 620

Cys Gly Ile Thr Ala Ile Gly Ile Phe Phe Leu Ile Val Phe Leu Leu
625                 630                 635                 640

Leu Leu Ala Ile Leu Leu Phe Phe Ala Val Lys Tyr Leu Leu Arg Trp
              645                 650                 655

Lys Tyr Gln His Ile
          660

(2) INFORMATION FOR SEQ ID NO:5:

(i) SEQUENCE CHARACTERISTICS:
        (A) LENGTH: 588 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 76..474

(xi) SEQUENCE DESCRIPTION: SEQ ID NO:5:

-continued

```
CGGCCAAAGA GGCCTAAACT TGCGGCTGTC CATCTCACCT ACAGCTCTGG TCTCATCCTC      60

AACTCAACCA CAATC ATG GCT CAG ATG ATG ACT CTG AGC CTC CTT AGC CTG     111
                 Met Ala Gln Met Met Thr Leu Ser Leu Leu Ser Leu
                  1               5                  10

GTC CTG GCT CTC TGC ATC CCC TGG ACC CAA GGC AGT GAT GGA GGG GGT      159
Val Leu Ala Leu Cys Ile Pro Trp Thr Gln Gly Ser Asp Gly Gly Gly
            15                  20                  25

CAG GAC TGC TGC CTT AAG TAC AGC CAG AAG AAA ATT CCC TAC AGT ATT      207
Gln Asp Cys Cys Leu Lys Tyr Ser Gln Lys Lys Ile Pro Tyr Ser Ile
        30                  35                  40

GTC CGA GGC TAT AGG AAG CAA GAA CCA AGT TTA GGC TGT CCC ATC CCG      255
Val Arg Gly Tyr Arg Lys Gln Glu Pro Ser Leu Gly Cys Pro Ile Pro
 45                  50                  55                  60

GCA ATC CTG TTC TCA CCC CGG AAG CAC TCT AAG CCT GAG CTA TGT GCA      303
Ala Ile Leu Phe Ser Pro Arg Lys His Ser Lys Pro Glu Leu Cys Ala
                65                  70                  75

AAC CCT GAG GAA GGC TGG GTG CAG AAC CTG ATG CGC CGC CTG GAC CAG      351
Asn Pro Glu Glu Gly Trp Val Gln Asn Leu Met Arg Arg Leu Asp Gln
            80                  85                  90

CCT CCA GCC CCA GGG AAA CAA AGC CCC GGC TGC AGG AAG AAC CGG GGA      399
Pro Pro Ala Pro Gly Lys Gln Ser Pro Gly Cys Arg Lys Asn Arg Gly
        95                  100                 105

ACC TCT AAG TCT GGA AAG AAA GGA AAG GGC TCC AAG GGC TGC AAG AGA      447
Thr Ser Lys Ser Gly Lys Lys Gly Lys Gly Ser Lys Gly Cys Lys Arg
    110                 115                 120

ACT GAA CAG ACA CAG CCC TCA AGA GGA TAGCCCAGTA GCCCGCCTGG            494
Thr Glu Gln Thr Gln Pro Ser Arg Gly
125                 130

AGCCCAGGAG ATCCCCCACG AACTTCAAGC TGGGTGGTTC ACGGTCCAAC TCACAGGCAA    554

AGAGGGAGCT AGAAAACAGA CTCAGGAGCC GCTA                                588

(2) INFORMATION FOR SEQ ID NO:6:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Gln Met Met Thr Leu Ser Leu Leu Ser Leu Val Leu Ala Leu
 1               5                  10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130
```

(2) INFORMATION FOR SEQ ID NO:7:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 67..348

(xi) SEQUENCE DESCRIPTION: SEQ ID NO:7:

```
CTTCCAAGAA GAGCAGCAAA GCTGAAGTAG CAGCAACAGC ACCAGCAGCA ACAGCAAAAA         60

ACAAAC ATG AGT GTG AAG GGC ATG GCT ATA GCC TTG GCT GTG ATA TTG          108
       Met Ser Val Lys Gly Met Ala Ile Ala Leu Ala Val Ile Leu
         1               5                  10

TGT GCT ACA GTT GTT CAA GGC TTC CCC ATG TTC AAA AGA GGA CGC TGT          156
Cys Ala Thr Val Val Gln Gly Phe Pro Met Phe Lys Arg Gly Arg Cys
 15              20                  25                  30

CTT TGC ATA GGC CCT GGG GTA AAA GCA GTG AAA GTG GCA GAT ATT GAG          204
Leu Cys Ile Gly Pro Gly Val Lys Ala Val Lys Val Ala Asp Ile Glu
                 35                  40                  45

AAA GCC TCC ATA ATG TAC CCA AGT AAC AAC TGT GAC AAA ATA GAA GTG          252
Lys Ala Ser Ile Met Tyr Pro Ser Asn Asn Cys Asp Lys Ile Glu Val
             50                  55                  60

ATT ATT ACC CTG AAA GAA AAT AAA GGA CAA CGA TGC CTA AAT CCC AAA          300
Ile Ile Thr Leu Lys Glu Asn Lys Gly Gln Arg Cys Leu Asn Pro Lys
         65                  70                  75

TCG AAG CAA GCA AGG CTT ATA ATC AAA AAA GTT GAA AGA AAG AAT TTT          348
Ser Lys Gln Ala Arg Leu Ile Ile Lys Lys Val Glu Arg Lys Asn Phe
     80                  85                  90

TAAAAATATC AAAACATATG AAGTCCTGGA AAAGGGCATC TGAAAAACCT AGAACAAGTT        408

TAACTGTGAC TACTGAAATG ACAAGAATTC TACAGTAGGA AACTGAGACT TTTCTATGGT        468

TTTGTGACTT TCAACTTTTG TACAGTTATG TGAAGGATGA AAGGTGGGTG AAAGGACCAA        528

AAACAGAAAT ACAGTCTTCC TGAATGAATG ACAATCAGAA TTCCACTGCC CAAAGGAGTC        588

CAACAATTAA ATGGATTTCT AGGAAAAGCT ACCTTAAGAA AGGCTGGTTA CCATCGGAGT        648

TTACAAAGTG CTTTCACGTT CTTACTTGTT GTATTATACA TTCATGCATT TCTAGGCTAG        708

AGAACCTTCT AGATTTGATG CTTACAACTA TTCTGTTGTG ACTATGAGAA CATTTCTGTC        768

TCTAGAAGTT ATCTGTCTGT ATTGATCTTT ATGCTATATT ACTATCTGTG GTTACAGTGG        828

AGACATTGAC ATTATTACTG GAGTCAAGCC CTTATAAGTC AAAAGCACCT ATGTGTCGTA        888

AAGCATTCCT CAAACATTTA AAAAAAAAA AAAAAAAAA AAAAAAAAA AAAAAAAAA            948

AAAAAAAAAA AAAAAAA                                                      966
```

(2) INFORMATION FOR SEQ ID NO:8:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Val Lys Gly Met Ala Ile Ala Leu Ala Val Ile Leu Cys Ala
 1               5                  10                  15

Thr Val Val Gln Gly Phe Pro Met Phe Lys Arg Gly Arg Cys Leu Cys
             20                  25                  30

Ile Gly Pro Gly Val Lys Ala Val Lys Val Ala Asp Ile Glu Lys Ala
         35                  40                  45

Ser Ile Met Tyr Pro Ser Asn Asn Cys Asp Lys Ile Glu Val Ile Ile
 50                  55                  60

Thr Leu Lys Glu Asn Lys Gly Gln Arg Cys Leu Asn Pro Lys Ser Lys
 65                  70                  75                  80

Gln Ala Arg Leu Ile Ile Lys Lys Val Glu Arg Lys Asn Phe
             85                  90
```

(2) INFORMATION FOR SEQ ID NO:9:

(i) SEQUENCE CHARACTERISTICS:
        (A) LENGTH: 1354 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 75..356

(xi) SEQUENCE DESCRIPTION: SEQ ID NO:9:

```
TTCTACTCCT TCCAAGAAGA GCAGCAAAGC TGAAGTAGCA GCAACAGCAC CAGCAGCAAC      60

AGCAAAAAAC AAAC ATG AGT GTG AAG GGC ATG GCT ATA GCC TTG GCT GTG      110
              Met Ser Val Lys Gly Met Ala Ile Ala Leu Ala Val
               1               5                  10

ATA TTG TGT GCT ACA GTT GTT CAA GGC TTC CCC ATG TTC AAA AGA GGA      158
Ile Leu Cys Ala Thr Val Val Gln Gly Phe Pro Met Phe Lys Arg Gly
         15                  20                  25

CGC TGT CTT TGC ATA GGC CCT GGG GTA AAA GCA GTG AAA GTG GCA GAT      206
Arg Cys Leu Cys Ile Gly Pro Gly Val Lys Ala Val Lys Val Ala Asp
     30                  35                  40

ATT GAG AAA GCC TCC ATA ATG TAC CCA AGT AAC AAC TGT GAC AAA ATA      254
Ile Glu Lys Ala Ser Ile Met Tyr Pro Ser Asn Asn Cys Asp Lys Ile
 45                  50                  55                  60

GAA GTG ATT ATT ACC CTG AAA GAA AAT AAA GGA CAA CGA TGC CTA AAT      302
Glu Val Ile Ile Thr Leu Lys Glu Asn Lys Gly Gln Arg Cys Leu Asn
                 65                  70                  75

CCC AAA TCG AAG CAA GCA AGG CTT ATA ATC AAA AAA GTT GAA AGA AAG      350
Pro Lys Ser Lys Gln Ala Arg Leu Ile Ile Lys Lys Val Glu Arg Lys
             80                  85                  90

AAT TTT TAAAAATATC AAAACATATG AAGTCCTGGA AAAGGGCATC TGAAAAACCT      406
Asn Phe
AGAACAAGTT TAACTGTGAC TACTGAAATG ACAAGAATTC TACAGTAGGA AACTGAGACT      466

TTTCTATGGT TTTGTGACTT TCAACTTTTG TACAGTTATG TGAAGGATGA AAGGTGGGTG      526

AAAGGACCAA AAACAGAAAT ACAGTCTTCC TGAATGAATG ACAATCAGAA TTCCACTGCC      586

CAAAGGAGTC CAACAATTAA ATGGATTTCT AGGAAAAGCT ACCTTAAGAA AGGCTGGTTA      646

CCATCGGAGT TTACAAAGTG CTTTCACGTT CTTACTTGTT GTATTATACA TTCATGCATT      706

TCTAGGCTAG AGAACCTTCT AGATTTGATG CTTACAACTA TTCTGTTGTG ACTATGAGAA      766

CATTTCTGTC TCTAGAAGTT ATCTGTCTGT ATTGATCTTT ATGCTATATT ACTATCTGTG      826

GTTACAGTGG AGACATTGAC ATTATTACTG GAGTCAAGCC CTTATAAGTC AAAAGCACCT      886
```

ATGTGTCGTA AAGCATTCCT CAAACATTTT TTCATGCAAA TACACACTTC TTTCCCCAAA    946

TATCATGTAG CACATCAATA TGTAGGGAAA CATTCTTATG CATCATTTGG TTTGTTTTAT   1006

AACCAATTCA TTAAATGTAA TTCATAAAAT GTACTATGAA AAAAATTATA CGCTATGGGA   1066

TACTGGCAAC AGTGCACATA TTTCATAACC AAATTAGCAG CACCGGTCTT AATTTGATGT   1126

TTTTCAACTT TTATTCATTG AGATGTTTTG AAGCAATTAG GATATGTGTG TTTACTGTAC   1186

TTTTTGTTTT GATCCGTTTG TATAAATGAT AGCAATATCT TGGACACATT TGAAATACAA   1246

AATGTTTTTG TCTACCAAAG AAAAATGTTG AAAAATAAGC AAATGTATAC CTAGCAATCA   1306

CTTTTACTTT TTGTAATTCT GTCTCTTAGA AAAATACATA ATCTAATT                1354

(2) INFORMATION FOR SEQ ID NO:10:

(i) SEQUENCE CHARACTERISTICS:
       (A) LENGTH: 94 amino acids
       (B) TYPE: amino acid
       (D) TOPOLOGY: linear (ii) MOLECULE TYPE: protein (xi) SEQUENCE DESCRIPTION: SEQ ID NO:10:

```
Met Ser Val Lys Gly Met Ala Ile Ala Leu Ala Val Ile Leu Cys Ala
 1               5                  10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```

(2) INFORMATION FOR SEQ ID NO:11:

(i) SEQUENCE CHARACTERISTICS:
       (A) LENGTH: 813 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (ix) FEATURE:
       (A) NAME/KEY: CDS
       (B) LOCATION: 86..544

(xi) SEQUENCE DESCRIPTION: SEQ ID NO:11:

```
GGGAAGATAC ATTCACAGAA AGAGCTTCCT GCACAAAGTA AGCCACCAGC GCAACATGAC       60

AGTGAAGACC CTGCATGGCC CAGCC ATG GTC AAG TAC TTG CTG CTG TCG ATA       112
                            Met Val Lys Tyr Leu Leu Leu Ser Ile
                             1               5

TTG GGG CTT GCC TTT CTG AGT GAG GCG GCA GCT CGG AAA ATC CCC AAA       160
Leu Gly Leu Ala Phe Leu Ser Glu Ala Ala Ala Arg Lys Ile Pro Lys
 10                  15                  20                  25

GTA GGA CAT ACT TTT TTC CAA AAG CCT GAG AGT TGC CCG CCT GTG CCA       208
Val Gly His Thr Phe Phe Gln Lys Pro Glu Ser Cys Pro Pro Val Pro
                30                  35                  40
```

```
GGA GGT AGT ATG AAG CTT GAC ATT GGC ATC ATC AAT GAA AAC CAG CGC        256
Gly Gly Ser Met Lys Leu Asp Ile Gly Ile Ile Asn Glu Asn Gln Arg
            45                  50                  55

GTT TCC ATG TCA CGT AAC ATC GAG AGC CGC TCC ACC TCC CCC TGG AAT        304
Val Ser Met Ser Arg Asn Ile Glu Ser Arg Ser Thr Ser Pro Trp Asn
        60                  65                  70

TAC ACT GTC ACT TGG GAC CCC AAC CGG TAC CCC TCG GAA GTT GTA CAG        352
Tyr Thr Val Thr Trp Asp Pro Asn Arg Tyr Pro Ser Glu Val Val Gln
 75                  80                  85

GCC CAG TGT AGG AAC TTG GGC TGC ATC AAT GCT CAA GGA AAG GAA GAC        400
Ala Gln Cys Arg Asn Leu Gly Cys Ile Asn Ala Gln Gly Lys Glu Asp
 90                  95                 100                 105

ATC TCC ATG AAT TCC GTT CCC ATC CAG CAA GAG ACC CTG GTC GTC CGG        448
Ile Ser Met Asn Ser Val Pro Ile Gln Gln Glu Thr Leu Val Val Arg
            110                 115                 120

AGG AAG CAC CAA GGC TGC TCT GTT TCT TTC CAG TTG GAG AAG GTG CTG        496
Arg Lys His Gln Gly Cys Ser Val Ser Phe Gln Leu Glu Lys Val Leu
        125                 130                 135

GTG ACT GTT GGC TGC ACC TGC GTC ACC CCT GTC ATC CAC CAT GTG CAG        544
Val Thr Val Gly Cys Thr Cys Val Thr Pro Val Ile His His Val Gln
    140                 145                 150

TAAGAGGTGC ATATCCACTC AGCTGAAGAA GCTGTAGAAA TGCCACTCCT TACCCAGTGC       604

TCTGCAACAA GTCCTGTCTG ACCCCCAATT CCCTCCACTT CACAGGACTC TTAATAAGAC       664

CTGCACGGAT GGAAACAGAA AATATTCACA ATGTATGTGT GTATGTACTA CACTTTATAT       724

TTGATATCTA AATGTTAGG AGAAAAATTA ATATATTCAG TGCTAATATA ATAAAGTATT        784

AATAATTTAA AAATAAAAAA AAAAAAAA                                          813

(2) INFORMATION FOR SEQ ID NO:12:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:12:

Met Val Lys Tyr Leu Leu Leu Ser Ile Leu Gly Leu Ala Phe Leu Ser
 1               5                  10                  15

Glu Ala Ala Arg Lys Ile Pro Lys Val Gly His Thr Phe Phe Gln
             20                  25                  30

Lys Pro Glu Ser Cys Pro Val Pro Gly Gly Ser Met Lys Leu Asp
         35                  40                  45

Ile Gly Ile Ile Asn Glu Asn Gln Arg Val Ser Met Ser Arg Asn Ile
 50                  55                  60

Glu Ser Arg Ser Thr Ser Pro Trp Asn Tyr Thr Val Thr Trp Asp Pro
 65                  70                  75                  80

Asn Arg Tyr Pro Ser Glu Val Val Gln Ala Gln Cys Arg Asn Leu Gly
             85                  90                  95

Cys Ile Asn Ala Gln Gly Lys Glu Asp Ile Ser Met Asn Ser Val Pro
            100                 105                 110

Ile Gln Gln Glu Thr Leu Val Val Arg Arg Lys His Gln Gly Cys Ser
        115                 120                 125

Val Ser Phe Gln Leu Glu Lys Val Leu Val Thr Val Gly Cys Thr Cys
    130                 135                 140

Val Thr Pro Val Ile His His Val Gln
145                 150
```

SECRETED PROTEINS

This application is a divisional of application Ser. No. 08/514,014, filed Aug. 11, 1995.

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered factor (i.e., partial DNA/amino acid sequence of the factor in the case of hybridization cloning; activity of the factor in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for factors that are known to have biological activity by virtue of their secreted nature in the case of leader sequence cloning, or by virtue of the cell or tissue source in the case of PCR-based techniques. It is to these factors and the polynucleotides encoding them that the present invention is directed.

SUMMARY

In one embodiment, the present invention provides a composition comprising an isolated polynucleotide selected from the group consisting of:
 (a) a polynucleotide comprising the nucleotide sequence of SEQ ID NO:1 from nucleotide 38 to nucleotide 1447;
 (b) a polynucleotide comprising a fragment of the nucleotide sequence of SEQ ID NO:1 encoding a protein having biological activity;
 (c) a polynucleotide encoding a protein comprising the amino acid sequence of SEQ ID NO:2;
 (d) a polynucleotide encoding a protein comprising a fragment of the amino acid sequence of SEQ ID NO:2 having biological activity;
 (e) a polynucleotide which is an allelic variant of SEQ ID NO:1; and
 (f) a polynucleotide capable of hybridizing under stringent conditions to any one of the polynucleotides specified in (a)–(e).

In another embodiment, the present invention provides a composition comprising an isolated polynucleotide selected from the group consisting of:
 (a) a polynucleotide comprising the nucleotide sequence of SEQ ID NO:3 from nucleotide 52 to nucleotide 2034;
 (b) a polynucleotide comprising a fragment of the nucleotide sequence of SEQ ID NO:3 encoding a protein having biological activity;
 (c) a polynucleotide encoding a protein comprising the amino acid sequence of SEQ ID NO:4;
 (d) a polynucleotide encoding a protein comprising a fragment of the amino acid sequence of SEQ ID NO:4 having biological activity:
 (e) a polynucleotide which is an allelic variant of SEQ ID NO:4; and
 (f) a polynucleotide capable of hybridizing under stringent conditions to any one of the polynucleotides specified in (a)–(e).

In another embodiment, the present invention provides a composition comprising an isolated polynucleotide selected from the group consisting of:
 (a) a polynucleotide comprising the nucleotide sequence of SEQ ID NO:5 from nucleotide 76 to nucleotide 474;
 (b) a polynucleotide comprising a fragment of the nucleotide sequence of SEQ ID NO:5 encoding a protein having biological activity;
 (c) a polynucleotide encoding a protein comprising the amino acid sequence of SEQ ID NO:6;
 (d) a polynucleotide encoding a protein comprising a fragment of the amino acid sequence of SEQ ID NO:6 having biological activity;
 (e) a polynucleotide which is an allelic variant of SEQ ID NO:5; and
 (f) a polynucleotide capable of hybridizing under stringent conditions to any one of the polynucleotides specified in (a)–(e).

In another embodiment, the present invention provides a composition comprising an isolated polynucleotide selected from the group consisting of:
 (a) a polynucleotide comprising the nucleotide sequence of SEQ ID NO:7 from nucleotide 67 to nucleotide 348;
 (b) a polynucleotide comprising a fragment of the nucleotide sequence of SEQ ID NO:7 encoding a protein having biological activity;
 (c) a polynucleotide encoding a protein comprising the amino acid sequence of SEQ ID NO:8;
 (d) a polynucleotide encoding a protein comprising a fragment of the amino acid sequence of SEQ ID NO:8 having biological activity;
 (e) a polynucleotide which is an allelic variant of SEQ ID NO:7; and
 (f) a polynucleotide capable of hybridizing under stringent conditions to any one of the polynucleotides specified in (a)–(e).

In another embodiment, the present invention provides a composition comprising an isolated polynucleotide selected from the group consisting of:
 (a) a polynucleotide comprising the nucleotide sequence of SEQ ID NO:9 from nucleotide 75 to nucleotide 356;
 (b) a polynucleotide comprising a fragment of the nucleotide sequence of SEQ ID NO:9 encoding a protein having biological activity;
 (c) a polynucleotide encoding a protein comprising the amino acid sequence of SEQ ID NO:10;
 (d) a polynucleotide encoding a protein comprising a fragment of the amino acid sequence of SEQ ID NO:10 having biological activity;
 (e) a polynucleotide which is an allelic variant of SEQ ID NO:9; and
 (f) a polynucleotide capable of hybridizing under stringent conditions to any one of the polynucleotides specified in (a)–(e).

In another embodiment, the present invention provides a composition comprising an isolated polynucleotide selected from the group consisting of:

(a) a polynucleotide comprising the nucleotide sequence of SEQ ID NO:11 from nucleotide 86 to nucleotide 544;

(b) a polynucleotide comprising a fragment of the nucleotide sequence of SEQ ID NO:11 encoding a protein having biological activity;

(c) a polynucleotide encoding a protein comprising the amino acid sequence of SEQ ID NO:12;

(d) a polynucleotide encoding a protein comprising a fragment of the amino acid sequence of SEQ ID NO:12 having biological activity;

(e) a polynucleotide which is an allelic variant of SEQ ID NO:11; and (f) a polynucleotide capable of hybridizing under stringent conditions to any one of the polynucleotides specified in (a)–(e).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention.

Compositions comprising a protein biological activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:8;

(h) fragments of the amino acid sequence of SEQ ID NO:8;

(i) the amino acid sequence of SEQ ID NO:12; and (j) fragments of the amino acid sequence of SEQ ID NO:12; the protein being substantially free from other mammalian proteins.

Such compositions may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

Isolated Proteins and Polynucleotides

Figure 1:
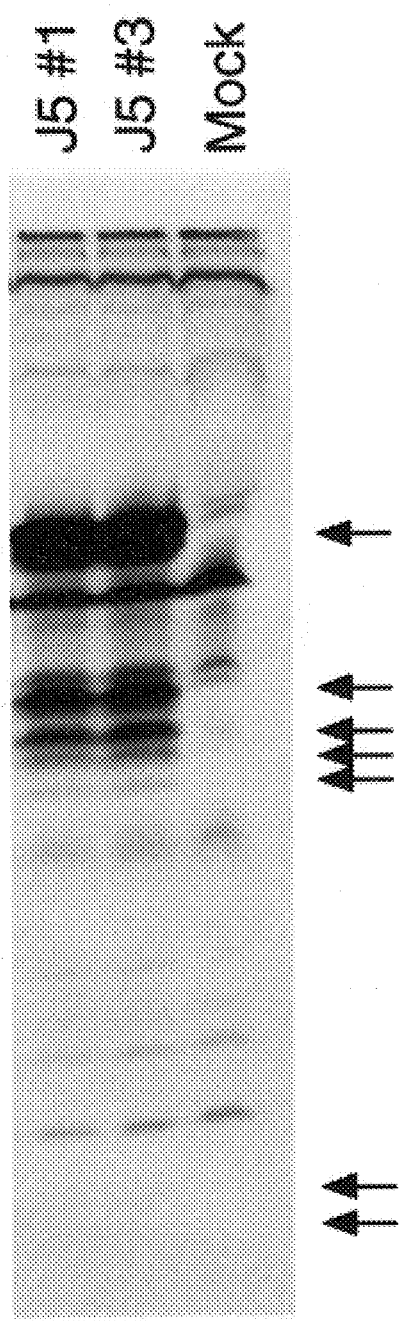
FIG. 1 is an autoradiograph evidencing the expression of clone J5 in COS cells (indicated by arrows). J5 is processed into multiple bands, with the major band at approximately 58 kD.

The sequence of a polynucleotide encoding one protein of the present invention is set forth in SEQ ID NO:1, with the coding region extending from nucleotides 38 to 1147. This polynucleotide has been identified as "clone J5" The amino acid sequence of the protein encoded by clone J5 is set forth in SEQ ID NO:2. Clone J5 was deposited with the American Type Culture Collection on Aug. 11, 1995 and given the accession number ATCC 69885. SEQ ID NO:1 represents a spliced combination of sequence obtained from an isolated clone identified as "J5_3_fl", with additional 5' sequence obtained from a second double stranded clone. Clone J5 was isolated from a human activated peripheral blood mononuclear cell (PBMC) library using a trap which selects for nucleotides encoding secreted proteins; therefore, clone J5 does encode a secreted factor. J5 encodes a novel protein; BLASTN/BLASTX or FASTA searches revealed no exact sequence matches. However, a BLASTX search revealed homology between the J5 protein (in the approximate region of amino acids 62–129 of SEQ ID NO:2), epididymal apical proteins (including without limitation, epididymal apical protein I-precursor (*Macaca fascicularis*) (accession X66139)) and several snake venom haemorrhagic peptides (disintegrins) (including without limitation those assigned accession U01235-1237, X68251, and M89784). Analysis of the full-length J5 sequences revealed that the disintegrin domain was incomplete and that this clone did not contain an EGF-domain, as with some of the other disintegrin family members. J5 does contain a conserved metallo-proteinase domain. Based upon these homologies, J5 and these homologous proteins are expected to share at least some activities.

The sequence of a polynucleotide encoding another protein of the present invention is set forth in SEQ ID NO:3, with the coding region extending from nucleotides 52 to 2034. This polynucleotide has been identified as "clone J422" The amino acid sequence of the protein encoded by clone J422 is set forth in SEQ ID NO:4. Clone J422 was deposited with the American Type Culture Collection on Aug. 11, 1995 and given the accession number ATCC 69884. SEQ ID NO:3 represents a spliced combination of sequence obtained from an isolated clone identified as "J422_fl", with additional 5' sequence obtained from a second double stranded clone. Clone J422 was isolated from a human activated peripheral blood mononuclear cell (PBMC) library using a trap which selects for nucleotides encoding secreted proteins; therefore, clone J422 does encode a secreted factor. J422 encodes a novel protein; BLASTN/BLASTX or FASTA searches revealed no exact sequence matches. However, a FASTA search revealed homology between the J422 protein (in the approximate region of amino acids 34–156 of SEQ ID NO:4) and a number of Drosophila leucine-rich repeat (LRR) proteins. Analysis of the full-length J422 sequences revealed that the conserved EGF-domain found in a number of LRR family members was not present in J422. Based upon these homologies, J422 and these homologous proteins are expected to share at least some activities.

The sequence of a polynucleotide encoding another protein of the present invention is set forth in SEQ ID NO:5, with the coding region extending from nucleotides 76 to 474. This polynucleotide has been identified as "clone L105" The amino acid sequence of the protein encoded by clone L105 is set forth in SEQ ID NO:6. Clone L105 was deposited with the American Type Culture Collection on Aug. 11, 1995 and given the accession number ATCC 69883. Clone L105 was isolated from a murine adult thymus library using a trap which selects for nucleotides encoding secreted proteins; therefore, clone L105 does encode a secreted factor. L105 encodes a novel protein; BLASTN/BLASTX or FASTA searches revealed no exact sequence matches. However, a BLASTX search revealed homology between the L105 protein (particularly in the approximate region of amino acids 73–91 of SEQ ID NO:6), various monocyte and other chemoattractant proteins (including without limitation those assigned accession M577441, X71087, X72308, X14768 and M24545) and a chicken (Gallus gallus) cytokine (accession L34553). Based upon these homologies, L105 and these homologous proteins are expected to share at least some activities.

The sequence of polynucleotides encoding another protein of the present invention is set forth in SEQ ID NO:7 and SEQ ID NO:9, with the coding regions extending from nucleotides 67 to 348 and nucleotides 75 to 356, respectively. These polynucleotides have been identified as "clone H174-10" and "clone H174-43", respectively (collectively referred to herein as "H174"). The amino acid sequence of the protein encoded by clones H174 is set forth in SEQ ID NO:8 and SEQ ID NO:10. Clone H174 was deposited with the American Type Culture Collection on Aug. 11, 1995 and given the accession number ATCC 69882. Clones H174 were isolated from a human activated peripheral blood mononuclear cell (PBMC) library using a trap which selects for nucleotides encoding secreted proteins; therefore, H174 does encode a secreted factor. H174 encodes a novel protein; BLASTN/BLASTX or FASTA searches revealed no exact sequence matches. However, a BLASTX search revealed homology between the H174 protein, human IP-10 (accession M33266) and murine CRG-2 (accession M86820) (species homologs). Based upon these homologies, H174 and these homologous proteins are expected to share at least some activities.

The sequence of a polynucleotide encoding another protein of the present invention is set forth in SEQ ID NO:11, with the coding region extending from nucleotides 86 to 544. This polynucleotide has been identified as "B18" The amino acid sequence of the protein encoded by clone B18 is set forth in SEQ ID NO:12. Clone B18 was deposited with the American Type Culture Collection on Jul. 6, 1995 and assigned accession number ATCC 69868. Clone B18 was isolated from a human activated peripheral blood mononuclear cell (PBMC) library using a trap which selects for nucleotides encoding secreted proteins; therefore, clone B18 does encode a secreted factor. B18 encodes a novel protein; BLASTN/BLASTX or FASTA searches revealed no exact sequence matches. However, a BLASTX search revealed that the region from amino acid 29 to amino acid 163 of B18 (SEQ ID NO:12) shows marked homology to portions of murine CTLA-8 (amino acids 18 to 150, accession L13839) and herpesvirus Saimiri ORF13 ("herpes CTLA-8") (amino acids 19 to 151, accession X64346). Based upon these homologies, B18 is believed to be the human homolog of murine and herpes CTLA-8 (i.e., "human CTLA-8"). B18 may demonstrate proinflammatory activity, particularly in development of T-cell dependent immune responses. B18 is also expected to possess other activities specified herein.

Figure 2:
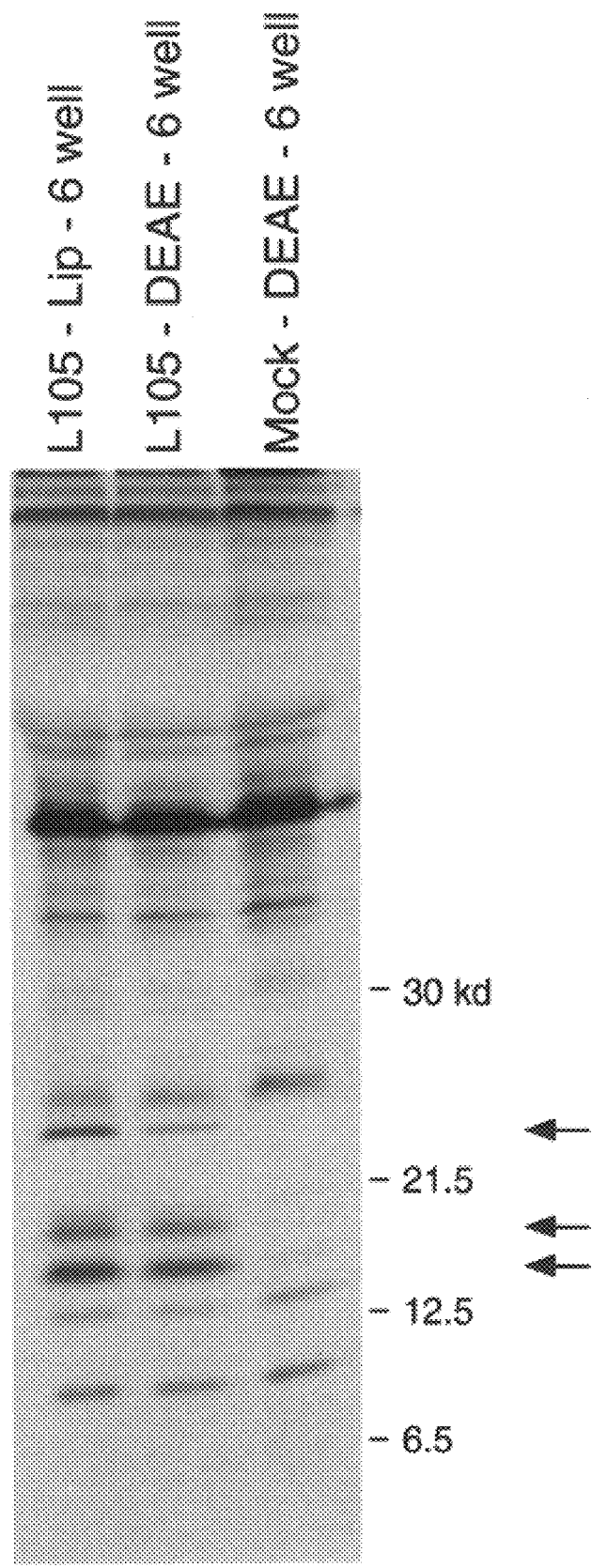
FIG. 2 is an autoradiograph evidencing the expression of clone L105 in COS cells (indicated by arrows).
Figure 3:
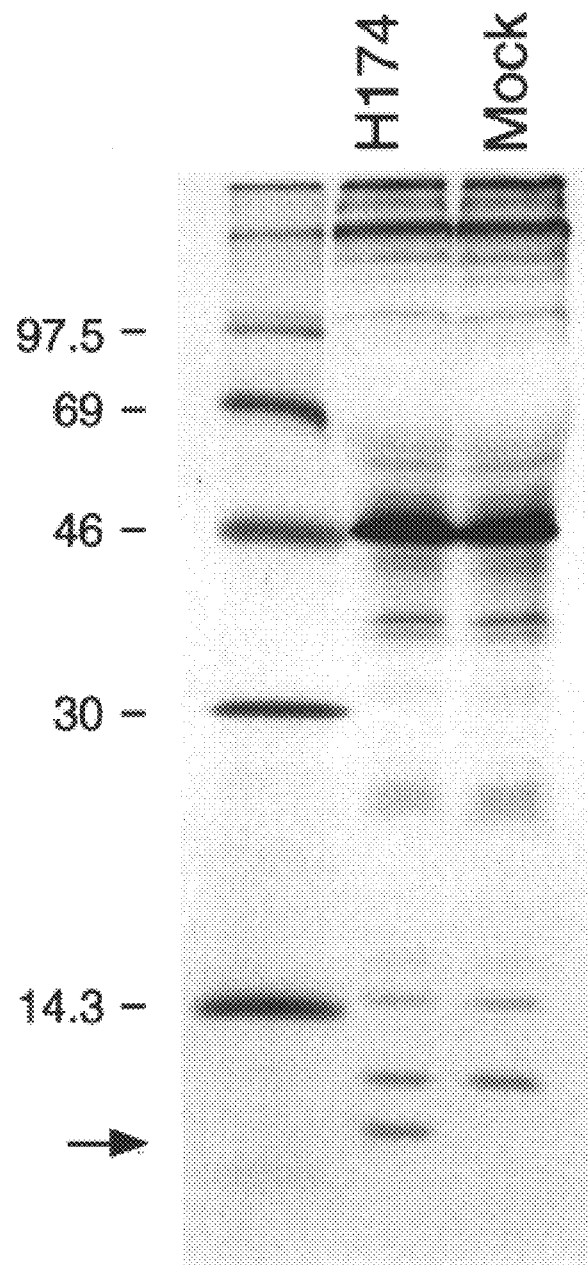
FIG. 3 is an autoradiograph evidencing the expression of clone H174 in COS cells (indicated by arrows).
Figure 4:
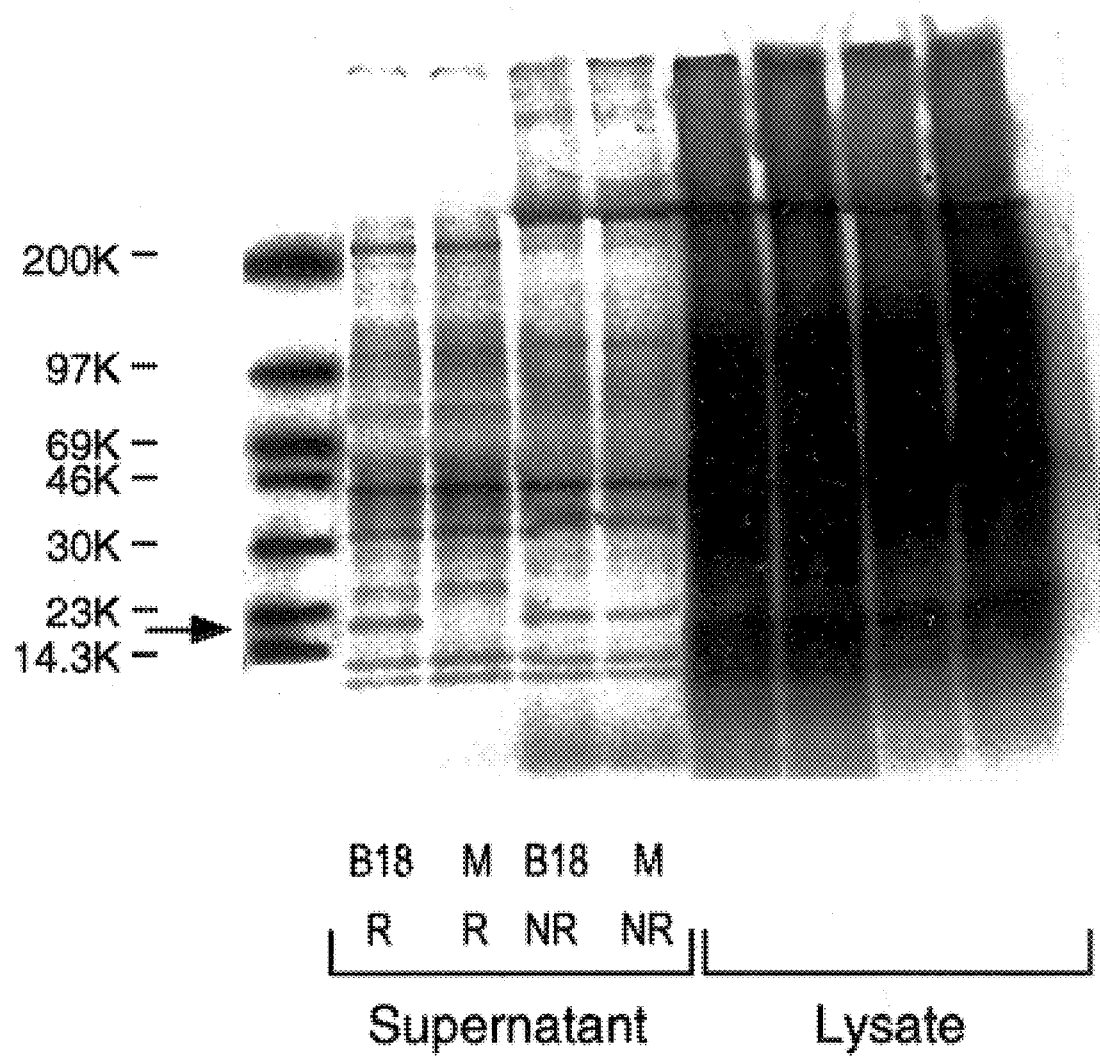
FIG. 4 is an autoradiograph evidencing the expression of clone B18 in COS cells (indicated by arrows).

Clones J5, L105, H174 and B18 were each transfected into COS cells labelled with $^{35}$S-methionine and protein was expressed. Autoradiographs evidencing expression of the proteins in conditioned media are presented in FIGS. 1, 2, 3 and 4, respectively. The bands of protein expressed from the relevant clone are indicated by arrows.

Polynucleotides hybridizing to the polynucleotides of the present invention under stringent conditions and highly stringent conditions are also part of the present invention. As used herein, "highly stringent conditions" include, for example, at least about 0.2×SSC at 65° C.; and "stringent conditions" include, for example, at least about 4×SSC at 65° C. or at least about 50% formamide, 4×SSC at 42° C. Allelic variants of the polynucleotides of the present invention are also encompassed by the invention.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin* No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides of the present invention and the proteins encoded thereby are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Tool Utility

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers (when labeled) to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used to raise antibodies or to elicit another immune response; as a reagent (including the labelled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these "research tool" utilities are capable of being developed into reagent grade or kit format for commercialization as "research products."

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152:1756–1761, 1994.

Assays for cytokine production and/or proliferation of spleen cells, lymph node cells or thymocytes include, without limitation, those described in: Polyclonal T cell stimulation, Kruisbeek A. M. and Shevach, E. M. In *Current Protocols in Immunology.* J.E.e.a. Coligan eds. Vol 1 pp. 3.12.1–3.12.14, John Wiley and Sons, Toronto. 1994; and Measurement of mouse and human Interferon γ, Schreiber, R. D. In *Current Protocols in Immunology.* J.E.e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology.* J.E.e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In *Current Protocols in Immunology.* J.E.e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11-Bennett, F., Giannotti, J., Clark, S. C. and Turner, K. J. In *Current Protocols in Immunology.* J.E.e.a. Coligan eds. Vol 1 pp. 6.15.1 John Wiley and Sons, Toronto. 1991; Measurement of mouse and human Interleukin 9-Ciarletta, A., Giannotti, J., Clark, S. C. and Turner, K. J. In *Current Protocols in Immunology.* J.E.e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober Pub. Greene Publishing Associates and Wiley-Interscience (Chapter 3. In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating/Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, leshmania, malaria and various fungal infections such as candida. Of course, in this regard, a protein of the present invention may also be useful where a boost to the immune system generally would be indicated, i.e., in the treatment of cancer.

Autoimmune disorders which may be treated using a protein of the present invention include, for example, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma or other respiratory problems. Other conditions, in which immune suppression is desired (including, for example, asthma and related respriatory conditions), may also be treatable using a protein of the present invention.

A protein of the present invention may also suppress chronic or acute inflammation, such as, for example, that associated with infection (such as septic shock or systemic inflammatory response syndrome (SIRS)), inflammatory bowel disease, Crohn's disease or resulting from over production of cytokines such as TNF or IL-1 (such as the effect demonstrated by IL-11).

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In *Current Protocols in Immunology.* J.E.e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by denritic cells that activate naive T-cells) include, without limitation, those described in: Guery et al., J. Immunol. 134:536–544, 1995; Inaba et al., Journal of Experimenal Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 1 72:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–88, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentarily to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e. in conjunction with bone marrow transplantation) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embyronic differentation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In *Culture of Hematopoietic Cells.* R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In *Culture of Hematopoietic Cells.* R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells.* R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells.* R. I. Freshney, et al. eds. Vol pp. 163–179, Wiley-Liss, Inc., New York, N.Y. 1994; Long term culture initating cell assay, Sutherland, H. J. In *Culture of Hematopoietic Cells.* R. I. Freshney, et al. eds. Vol pp. 139–162, Wiley-Liss, Inc., New York, N.Y. 1994.

Tissue Generation/Regeneration Activity

A protein of the present invention also may have utility in compositions used for bone, cartilage, tendon, ligament and/or nerve tissue growth or regeneration, as well as for wound healing and tissue repair, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

It is expected that a protein of the present invention may also exhibit activity for generation of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition of fibrotic scarring to allow normal tissue to regenerate.

A protein of the present invention may also be useful for gut protection or regeneration and treatment of lung or liver fibrosis, reperfusion injury in various tissues, and conditions resulting from systemic cytokine damage.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Activin/Inhibin Activity

A protein of the present invention may also exhbit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, neutrophils, T-cells, mast cells, eosinophils and/or endothelial cells. Chemotactic and chemokinetic proteins can be used to mobilized or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W.Strober, Pub. Greene Publishing Associates and Wiley-Intersciece (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction or stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity: of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W.Strober, Pub. Greene Publishing Associates and Wiley-Intersciece (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Other Activities

A protein of the invention may also exhibit one or more of the following additional activities or effects: killing infectious agents, including, without limitation, bacteria, viruses, fungi and other parasites; effecting (suppressing or enhancing) bodily characteristics, including, without limitation, height, weight, hair color, eye color, skin or other tissue pigmentation, or organ size (such as, for example, breast augmentation or diminution); effecting the processing of dietary fat, protein or carbohydrate; effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of ebryonic stem cells in lineages other than hematopoietic lineages; and in the case of enzymes, correcting deficiencies of the enzyme and treating related diseases.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface imrnunolgobu- lin and other molecules on B cells as well as antibodies able to bind the TCR and other molecules on T cells can be combined with the pharmaceutical compositon of the inven- tion.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is suffi- cient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simulta- neously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti- thrombotic factors, or sequentially. If administered sequentially, the attending physician will decide on the appropriate sequence of administering protein of the present invention in combination with cytokine(s), lymphokine(s), other hematopoietic factor(s), thrombolytic or anti- thrombotic factors.

Administration of protein of the present invention used in the pharmaceutical composition or to practice the method of the present invention can be carried out in a variety of conventional ways, such as oral ingestion, inhalation, or cutaneous, subcutaneous, or intravenous injection. Intrave- nous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may addi- tionally contain a solid carrier such as a gelatin or an adjuvant. The tablet, capsule, and powder contain from about 5 to 95% protein of the present invention, and pref- erably from about 25 to 90% protein of the present inven- tion. When administered in liquid form, a liquid carrier such as water, petroleum, oils of animal or plant origin such as peanut oil, mineral oil, soybean oil, or sesame oil, or synthetic oils may be added. The liquid form of the phar- maceutical composition may further contain physiological saline solution, dextrose or other saccharide solution, or glycols such as ethylene glycol, propylene glycol or poly- ethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chlo- ride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight.

The duration of intravenous therapy using the pharma- ceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present inven- tion.

Protein of the invention may also be used to immunize animals to obtain polyclonal and monoclonal antibodies which specifically react with the protein. Such antibodies may be obtained using either the entire protein or fragments thereof as an immunogen. The peptide immunogens addi- tionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGI I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. A protein produced according to a process comprising the following steps:
   (a) growing a culture of a host cell in a suitable culture medium; and
   (b) purifying the protein from the culture; wherein said host cell is transformed with an isolated polynucleotide operably linked to an expression control sequence, and wherein said polynucleotide is selected from the group consisting of:
      (i) a polynucleotide comprising the nucleotide sequence of SEQ ID NO:1 from nucleotide 38 to nucleotide 1447; and
      (ii a polynucleotide encoding a protein comprising the amino acid sequence of SEQ ID NO:2.

2. A composition comprising a protein, wherein said protein comprises the amino acid sequence of SEQ ID NO:2 the protein being substantially free from other mammalian proteins.

3. The protein of claim 1, wherein said polynucleotide comprises the nucleotide sequence of SEQ ID NO:1 from nucleotide 38 to nucleotide 1147.

4. The protein of claim 1, wherein said polynucleotide comprises a polynucleotide encoding a protein comprising the amino acid sequence of SEQ ID NO:2.

5. A protein produced according to a process comprising the following steps:
   (a) growing a culture of a host cell in a suitable culture medium; and
   (b) purifying the protein from the culture;
wherein said host cell is transformed with an isolated polynucleotide operably linked to an expression control sequence, and wherein said polynucleotide is selected from the group consisting of:
   (i) a polynucleotide comprising the nucleotide sequence of SEQ ID NO:3 from nucleotide 52 to nucleotide 2034; and
   (ii) a polynucleotide encoding a protein comprising the amino acid sequence of SEQ ID NO:4.

6. A composition comprising a protein, wherein said protein comprises the amino acid sequence of SEQ ID NO:4 the protein being substantially free from other mammalian proteins.

7. The protein of claim 5, wherein said polynucleotide comprises the nucleotide sequence of SEQ ID NO:3 from nucleotide 52 to nucleotide 2034.

8. The protein of claim 5, wherein said polynucleotide comprises a polynucleotide encoding a protein comprising the amino acid sequence of SEQ ID NO:4.

9. A protein produced according to a process comprising the following steps:
   (a) growing a culture of a host cell in a suitable culture medium; and
   (b) purifying the protein from the culture;
wherein said host cell is transformed with an isolated polynucleotide operably linked to an expression control sequence, and wherein said polynucleotide is selected from the group consisting of:
   (i) a polynucleotide comprising the nucleotide sequence of SEQ ID NO:5 from nucleotide 76 to nucleotide 474; and
   (ii) a polynucleotide encoding a protein comprising the amino acid sequence of SEQ ID NO:6.

10. A composition comprising a protein, wherein said protein comprises the amino acid sequence of SEQ ID NO:6 the protein being substantially free from other mammalian proteins.

11. The protein of claim 9, wherein said polynucleotide comprises the nucleotide sequence of SEQ ID NO:5 from nucleotide 76 to nucleotide 474.

12. The protein of claim 9, wherein said polynucleotide comprises a polynucleotide encoding a protein comprising the amino acid sequence of SEQ ID NO:6.

13. A protein produced according to a process comprising the following steps:
   (a) growing a culture of a host cell in a suitable culture medium; and
   (b) purifying the protein from the culture;
wherein said host cell is transformed with an isolated polynucleotide operably linked to an expression control sequence, and wherein said polynucleotide is selected from the group consisting of:
   (i) a polynucleotide comprising the nucleotide sequence of SEQ ID NO:7 from nucleotide 67 to nucleotide 348; and
   (ii) a polynucleotide encoding a protein comprising the amino acid sequence of SEQ ID NO:8.

14. A composition comprising a protein, wherein said protein comprises the amino acid sequence of SEQ ID NO:8 the protein being substantially free from other mammalian proteins.

15. The protein of claim 13, wherein said polynucleotide comprises the nucleotide sequence of SEQ ID NO:7 from nucleotide 67 to nucleotide 348.

16. The protein of claim 13, wherein said polynucleotide comprises a polynucleotide encoding a protein comprising the amino acid sequence of SEQ ID NO:8.

* * * * *